United States Patent [19]
Boutos

[11] Patent Number: 5,697,966
[45] Date of Patent: Dec. 16, 1997

[54] APPARATUS FOR STIMULATING LIVING TISSUE

[76] Inventor: David Boutos, 4420 Dunlap Crossing St., Las Vegas, Nev. 89129

[21] Appl. No.: 568,875

[22] Filed: Dec. 7, 1995

Related U.S. Application Data

[63] Continuation-in-part of Ser. No. 369,172, Jan. 5, 1995, Pat. No. 5,571,118.

[51] Int. Cl.$^6$ ................................................ A61N 1/05
[52] U.S. Cl. ................................................ 607/138
[58] Field of Search ........................ 607/138, 116, 607/143; 128/639, 644

[56] References Cited

U.S. PATENT DOCUMENTS

| | | | |
|---|---|---|---|
| 3,866,613 | 2/1975 | Kenny et al. | 128/834 |
| 5,383,923 | 1/1995 | Webster, Jr. | 607/125 |
| 5,456,709 | 10/1995 | Hamedi | 607/138 |

*Primary Examiner*—Scott Getzow
*Attorney, Agent, or Firm*—Meschkow and Gresham, P.L.C.

[57] ABSTRACT

Electrodes for stimulating living tissue such as penile, scrotal, anal, vaginal and clitoral tissue are shown. The electrodes are formed from elastomeric material. Electrical stimulation to such areas is intended to control incontinence, to induce penile erection, or to induce excitation and orgasm. A plug electrode formed from elastomeric material, has a nonconductive base plate and base, and a conductive portion comprising a stem extending from the base and the ellipsoid ball extending from the stem. A snap contact on the base plate allows the electrode to be connected to an electrical source, and a wire within the base terminating in the stem carries the electricity, when applied, from the contact to stem and to the ellipsoid ball. A memory wire is also shown allowing the ellipsoid ball to be bent along its length or allowing the stem to be bent against the base, thereby angling the posture of the ball relative the base. A tube electrode connects to an electrical source by a banana plug inserted into one its ends. The banana plug is wired to an electrical source. The tube electrode is electrically conductive along its entirety. A memory wire is also shown allowing the tube electrode to be bent along its length around a protrusion, or against a nonlinear surface and conform to that surface.

3 Claims, 1 Drawing Sheet

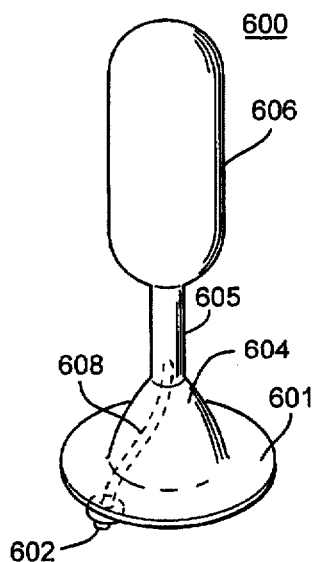
FIG. 1
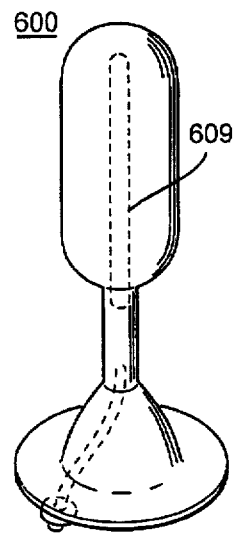
FIG. 2
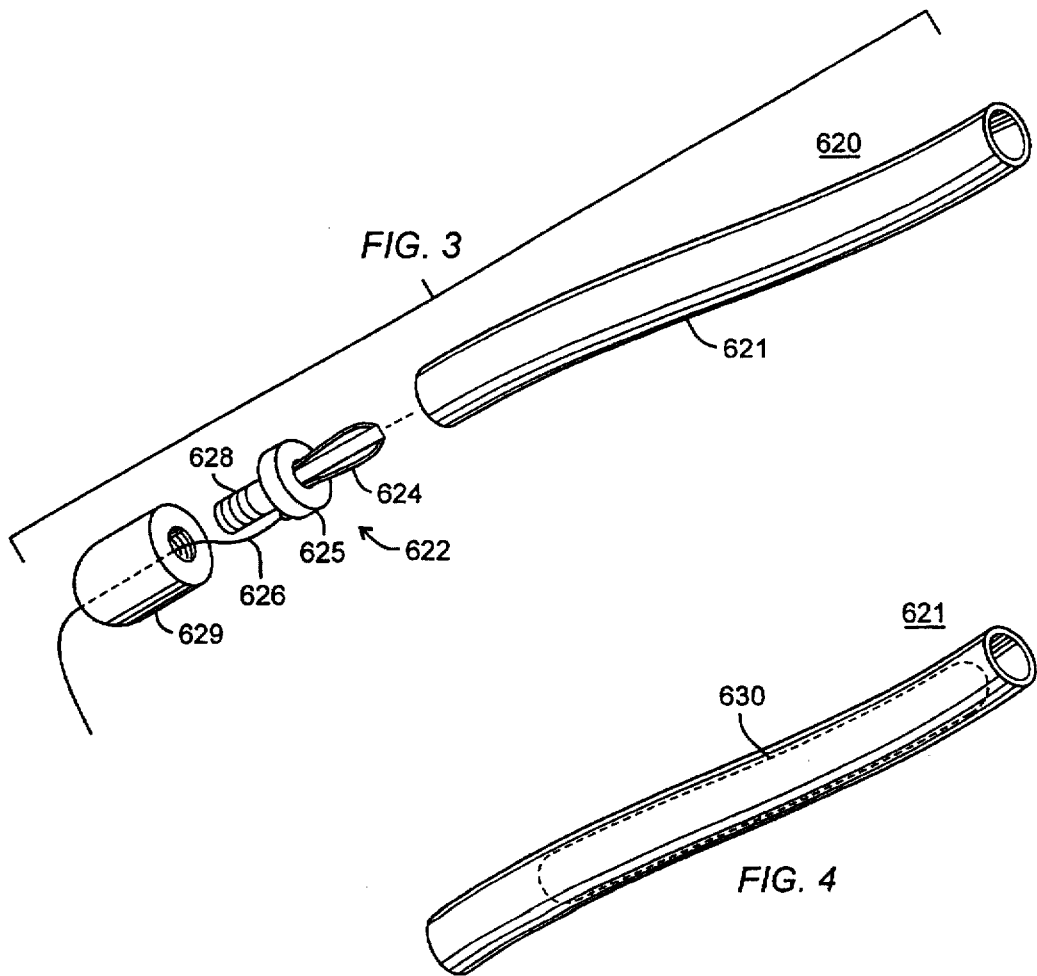
FIG. 3
FIG. 4

APPARATUS FOR STIMULATING LIVING TISSUE

RELATED APPLICATION

This application is a Continuation-In-Part of "Apparatus for Stimulating Penile, Scrotal, Anal, Vaginal and Clitoral Tissue," invented by David Boutos, Ser. No. 08/369,172, filed Jan. 5, 1995, now U.S. Pat. No. 5,571,118.

BACKGROUND OF THE INVENTION

1. Field of the Invention

This invention relates to apparatus for applying electrical energy to living tissue.

More particularly, the present invention relates to apparatus for electrically stimulating penile, scrotal, anal vaginal and clitoral tissue.

In a further and more specific aspects, the invention relates to electrically stimulating penile, scrotal, vaginal and clitoral tissue for the purposes of treating incontinence in men and women, and for inducing penile erection, male and female orgasm.

2. Prior Art

It is widely known that the application of electrical stimulation to certain neuromuscular areas in or near the genitalia can be used to treat incontinence in both men and women. Also known is that the application of electrical stimulation to penile tissue can cause erection where impotence may exist due to physiological or psychological conditions. Additionally it is known the application of electrical stimulation to penile, vaginal, clitoral, anal, or prostate tissue can induce orgasm, even where the subject has suffered vascular degenerative neural neuropathy. Finally it is known that diabetes and many other medical disorders can cause penile impotence.

The art is replete with various apparatus used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the vagina and the anus.

Urinary incontinence is a common problem that may require long term retraining of self-control, particularly after a stroke, or permanent use of an external control device. The prior art does not teach of apparatus that is designed to be worn while the user, fully dressed, moves about his or her everyday course of events.

Rigid rings are useable for males where the application of electrical current to only a portion of penile tissue is sufficient to induce urethral control or erection. This is because sufficient expansion room is required within the ring to accommodate penile engorgement. Rigid rings are particularly problematic where penile atrophy has occurred, and the desired goal is erection or orgasm. The tremendously varying size of the penile tissue from rest to engorgement may cause a need to use a large diameter ring on a small diameter penis, or to change rings during a treatment.

For the female, a discrete unit, usable in a variety of ways, is desirable to control incontinence, or to stimulate and to induce orgasm. Such a unit should be particularly designed to be worn under a user's clothing, and operative while the female was engaged in other normal everyday activity.

It would be highly advantageous, therefore, to remedy the foregoing and other deficiencies inherent in the prior art.

Accordingly, it is an object of the present invention to provide improvements in electrical stimulation apparatus for both men and women.

Another object of the invention is the provision of improvements especially adapted for use in connection with apparatus for controlling and treating incontinence in men and women.

And another object of the invention is to provide improved means for the application of electrical stimulation to the vagina.

Yet another object of the invention is to provide means for the application of electrical stimulation to the penile and scrotal tissue.

Yet still another object of the invention is the provision of improved means for the application of electrical stimulation to the penile and scrotal tissue that can expand with penile erection.

A further object of the instant invention is to provide improvements in the connectivity of electrical stimulation apparatus.

And a further object of the invention is the provision of a male and female electrical stimulation apparatus that can be worn comfortably and discretely under a user's clothing.

Yet a further object of this invention is to provide male electrical stimulation apparatus that can induce erection and orgasm, and female electrical stimulation apparatus that can induce orgasm.

And yet an object of the invention is the provision of means and improvements according to the foregoing which will materially reduce the cost of male and female electrical stimulation apparatus.

SUMMARY OF THE INVENTION

Briefly, to achieve the desired objects of the instant invention in accordance with a preferred embodiment thereof, first provided is a plug shaped electrode to which a source of electricity may be attached.

The plug shaped electrode is fabricated from elastomeric material. It may inserted into the vagina and positioned therein so that the application of electricity provided by the source connected to the electrode may contract the muscles surrounding the ureter, thereby controlling incontinence, or positioned therein so the application of electricity may induce excitation and orgasm.

It may also be inserted anally instead thereby stimulating that tissue and the nearby prostate for assisting in controlling incontinence, or for excitation. The plug electrode may include an internal wire so it can be bent and angled and retain the angled posture.

An electrode in the form of a tube for direct use or for to be wrapped around tissue such as penile and/or scrotal tissue comprises an alternate embodiment of the invention.

The tube is also formed from elastomeric material, and may have an internal wire so it can be bent and retain the bent position. An electrical plug, such as a banana plug having a plug end and a second end can be inserted in to an open end of the tube electrode to provide electricity from a source connected to the plug at its second end.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 1 is a perspective view of plug electrode in accordance with the present invention;

FIG. 2 is a view of plug electrode showing a position retaining wire mounted therein;

FIG. 3 is a perspective view of a tube electrode and its connector;

FIG. 4 is a view of the tube electrode showing a position retaining wire mounted therein.

PREFERRED EMBODIMENT OF THE PRESENT INVENTION

Turning now to the drawings in which like reference characters indicate corresponding elements throughout the several views, attention is first directed to FIG. 1 where plug electrode 600 is shown. Plug electrode 600 is fabricated from elastomeric material such as silicon, viton, and neoprene, and such material is non-conductive of electricity.

Plug electrode 600 has base plate 601, which has button snap male contact 602 embedded in it at the bottom. Rising from plate 601 is base 604. Extending therefrom is stem 605, and from there is generally ellipsoid ball-shaped electrode 606.

Electrode 606 and stem 605 are conductive of electricity. They are made conductive by embedding carbon particles in the silicon, viton, or neoprene during fabrication of plug electrode 600.

Both electrode 606 and stem 605 will conduct electricity when plug electrode 600 is connected to a source of electricity, typically a controller allowing for adjustment of current (not shown). The controller will typically include a jack, and a wire connected to the jack. The wire will typically terminate with a female snap connector. Such female snap connector is connected to snap connector 602.

Running directly to and connected to snap connector 602 is conductive line 608. Line 608 is simply conductive material running through the interior of base 604 and up into conductive stem 605, thereby carrying electricity provided by a controller to both conductive stem 605 and electrode 606.

In general use of plug electrode 600, electrode 606 and stem 605 are inserted vaginally or anally. Non-conductive base plate 601 and base 604 provide a stop to prevent too deep insertion, and a handle for moving or removing plug electrode 600 when inserted and electrified.

FIG. 2 shows an additional feature that may incorporated into plug electrode 600. Embedded within electrode 606 and stem 605 is wire 609. Wire 609 is not necessarily intended to carry electricity, but when within electrode 606 and stem 605, allows the bending of electrode 606 against stem 605, and retains the bent angle of electrode 606 relative to base 604. Wire 609 also allows the bending of electrode 606 along its ellipsoid ball shape, thereby retaining electrode 606 in a bent posture. Such bending and "memory" posturing allows plug electrode 600 to be effectively positioned within the cavity inserted.

Turning to FIG. 3, shown is tube electrode apparatus 620. Tube electrode apparatus 620, has tube electrode 621, and banana plug 622.

Tube electrode 621 is fabricated from carbon-imbedded elastomeric nonconductive material such as low modullus silicon, viton, and neoprene, thereby rending all of tube electrode 620 conductive. Tube electrode 621 is extremely flexible, and is generally analogous to spaghetti tubing. Banana plug 622 has plug end 624, made of three or four metal spring-like leafs joined at the top and terminating at base 625. Wire 626 is soldered to base 625.

Extending from base 625 is externally threaded stem 628. Wire 626 is run through internally threaded cap 629, and then cap 629 is screwed onto to stem 628 thereby insulating the base of banana plug 622. Wire 626 typically terminates at its other end (not shown) with a connector allowing it to connected to the jack of a controller (not shown).

When electricity is applied to tube electrode 621 its entire surface emanates current. When wire 630 is inserted within tube electrode 621, as shown in FIG. 4, it allows tube electrode 621 to be bent, and retain the bending posture. Tube electrode 621 can be coiled about any projection, i.e. a finger, or can be wrapped around and conform to the back of one's neck.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An electrode apparatus comprising:
    a tube shaped electrode having a length, and two ends at opposite ends of its length;
    an electrical contact that connects to one end of said tube; and
    a memory bend wire located within said tube electrode, said memory bend wire serving to substantially maintain a formed shape of said tube electrode.

2. The electrode apparatus of claim 1 wherein said tube shaped electrode is electrically conductive along its entire length.

3. The electrode apparatus of claim 1 wherein said tube electrode is elongated in an elongation direction parallel to its length, and said memory bend wire extends within said electrode substantially along said elongation direction.

* * * * *